US008231652B2

(12) United States Patent
Freed et al.

(10) Patent No.: US 8,231,652 B2
(45) Date of Patent: Jul. 31, 2012

(54) INSTRUMENT WITH SEALING DEVICE AND METHODS OF ADVANCING FLUID THERETHROUGH

(75) Inventors: David I. Freed, Westborough, MA (US); Malka S. Berndt, Lexington, MA (US); Michael J. Magill, Northborough, MA (US); Otto E. Anderhub, Miami, FL (US); Osiris A. Nunez, Hollywood, FL (US); Boris Kesler, Pembroke Pines, FL (US); Gerardo S. Martin, Hialeah, FL (US); Christopher D. Endara, Miami, FL (US); James M. Zardeskas, Pascoag, RI (US); Oscar Carrillo, Attleboro, MA (US); Satish Sharma, Randolph, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 2058 days.

(21) Appl. No.: 10/831,760

(22) Filed: Apr. 26, 2004

(65) Prior Publication Data

US 2005/0240218 A1 Oct. 27, 2005

(51) Int. Cl.
*A61B 17/00* (2006.01)
*A61B 18/18* (2006.01)
*A61B 17/32* (2006.01)
(52) U.S. Cl. ............................ 606/205; 606/51; 606/170

(58) Field of Classification Search .................... 606/51, 606/170, 205; 600/64, 566
See application file for complete search history.

(56) References Cited

U.S. PATENT DOCUMENTS

| 3,964,468 | A | | 6/1976 | Schulz |
| 5,295,956 | A | * | 3/1994 | Bales et al. ..................... 604/30 |
| 5,395,369 | A | | 3/1995 | McBrayer et al. |
| 5,489,290 | A | | 2/1996 | Furnish |
| 5,505,210 | A | | 4/1996 | Clement |
| 5,531,763 | A | * | 7/1996 | Mastri et al. .................. 606/148 |
| 5,810,876 | A | | 9/1998 | Kelleher |
| 7,399,272 | B2 | * | 7/2008 | Kim et al. ........................ 600/37 |

FOREIGN PATENT DOCUMENTS

| DE | 42 20 644 C1 | 1/1994 |
| EP | 0 736 285 A2 | 10/1996 |

OTHER PUBLICATIONS

International Search Report mailed Sep. 13, 2005 in International Application No. PCT/US2005/013577.

* cited by examiner

*Primary Examiner* — Gary Jackson
*Assistant Examiner* — Michael Mendoza
(74) *Attorney, Agent, or Firm* — Finnegan, Henderson, Farabow, Garrett & Dunner, LLP

(57) ABSTRACT

Embodiments of the invention include a medical instrument with a sealing device. In embodiments, the medical instrument is an endoscopic device having a seal between an elongate shaft member and/or on a portion of a handle to, for example, prevent flow communication between a lumen of the elongate member and the external environment.

34 Claims, 14 Drawing Sheets

INSTRUMENT WITH SEALING DEVICE AND METHODS OF ADVANCING FLUID THERETHROUGH

FIELD OF THE INVENTION

Embodiments of the invention include a medical instrument with a sealing device. In embodiments, the medical instrument is an endoscopic device having a seal between an elongate shaft member and/or on a portion of a handle to, for example, prevent flow communication between a lumen of the elongate member and the external environment.

BACKGROUND OF THE INVENTION

Various medical instruments may be used in connection with an endoscope for performing a number of operations at a site deep within a patient's body cavity. One such instrument, a biopsy forceps device, samples tissue from a body cavity with minimal intervention and discomfort to patients. Typically, a biopsy forceps device, like other endoscopic instruments, has a long flexible tubular member for insertion into a lumen of an endoscope. The tubular member is sufficiently long and flexible to follow a long, winding path of the body cavity. An end effector assembly, such as a biopsy forceps assembly, is attached at a distal end of the tubular member, and a handle is attached at a proximal end of the tubular member. The handle may have an elongate portion and a spool portion disposed around the elongate portion. The spool portion may be configured to move longitudinally relative to the elongate portion. An elongate mechanism, such as pull wires, extend through the tubular member to connect the end effector assembly to a hypotube. The hypotube is then connected to a portion of the handle, such as the spool portion. Longitudinal movement of the spool portion relative to the elongate portion of the handle causes the elongate mechanism to move longitudinally in the tubular member, which in turn causes the actuation of the end effector assembly.

In methods of using the biopsy forceps device, an endoscope is placed in a patient's body cavity adjacent to a tissue site from which the acquisition of a tissue sample is desired. The biopsy forceps device is then advanced to the tissue site via a working channel of the endoscope. Once the biopsy forceps device is next to the portion of the tissue from which the acquisition of a tissue sample is desired, the spool portion is moved relative to the elongate portion so as to move the hypotube and the pull wires. The movement of the hypotube and the pull wires causes the jaws of the biopsy forceps assembly to open. The open jaws are then advanced to the tissue site, and the spool portion is again moved relative to the elongate portion so as to move the hypotube and the pull wires such that the jaws close. The closing of the jaws causes a tissue sample to be lodged in the end effector assembly. The biopsy forceps device is then removed from the body cavity via the working channel of the endoscope.

During various endoscopic procedures, including biopsy procedures, the body cavity, such as the colon, may be insufflated to, for example, widen the organ so that the physician has a better view of the tissue site and/or the body cavity. Insufflation may be accomplished by forcing air into the body cavity, for example, before, during, or after advancing the biopsy forceps device into the endoscope and into the body cavity.

An endoscope typically includes appropriate seals to prevent the escape of the insufflated air out of the body cavity and to the external environment via the endoscope. In some cases, however, some of the air forced into the body cavity during insufflation escapes into the outside environment via the end effector assembly, the lumen of the elongate shaft member, and the handle assembly. This escape of air hinders the insufflation and the maintenance of the internal organ pressure. In addition, it can result in undesirable spraying of air or other gas or liquid into the operating room and onto those performing the procedure.

SUMMARY OF THE INVENTION

In accordance with the invention, an embodiment of the invention includes a medical device including a handle portion, an end effector assembly, an elongate member connecting the handle portion to the end effector assembly, and a sealing device associated with at least one of the handle portion and the elongate member to substantially prevent flow communication between a lumen of the elongate member and an environment external to the device.

Another embodiment of the invention includes a medical device including a handle portion, an elongate member extending from the handle portion, and a sealing device associated with at least one of the handle portion and the elongate member to substantially prevent flow communication between a lumen of the elongate member and an environment external to the device.

A further embodiment of the invention includes a method of advancing fluid through a medical device. The method includes providing a medical device having a handle portion, an elongate member extending from the handle portion, and a sealing device associated with at least one of the handle portion and the elongate member to substantially prevent flow communication between a lumen of the elongate member and an environment external to the device, and bypassing the sealing device to advance fluid through the lumen of elongate member.

In various embodiments, the invention may include additional features. For example, the handle portion may include a tube in flow communication with the elongate member. In another example, the sealing device may be configured to substantially prevent fluid flow through a gap between the tube and the elongate member. In a further example, the tube may be configured to be in flow communication with the environment external to the device via a proximal end of the tube. In yet another example, the sealing device may be configured to substantially prevent fluid flow through the elongate member. In still another example, a method may include placing a vessel containing fluid into the medical device and injecting fluid into the medical device.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

The foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate embodiments of the invention and together with the description, serve to explain the principles of the invention.

DESCRIPTION OF THE EMBODIMENTS

Reference will now be made in detail to the present exemplary embodiments of the invention illustrated in the accompanying drawings. Wherever possible, the same reference numbers will be used throughout the drawings to refer to the same or like parts.

Figure 1:
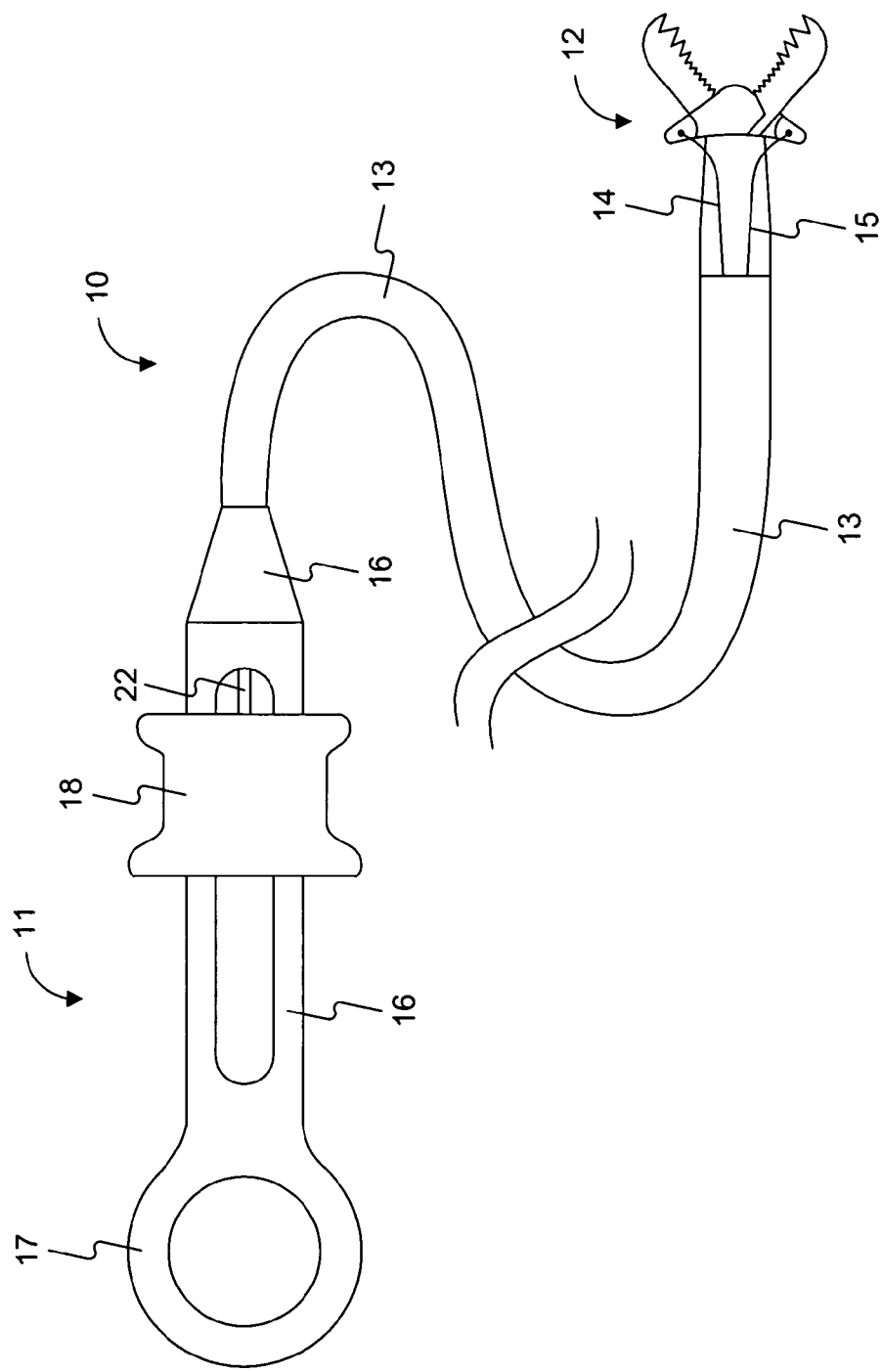
FIG. 1 is a perspective view of an exemplary endoscopic instrument.

An exemplary embodiment of an endoscopic instrument 10 is depicted in FIG. 1. The endoscopic instrument 10 includes a handle portion 11 and an end effector assembly 12 connected to each other by a flexible elongate member 13. Control wires 14, 15 extend between the handle portion 11 and the end effector assembly 12 via a lumen the flexible elongate member 13. The handle portion 11 includes an elongate portion 16 connected at its proximal end to a ring portion 17 and a spool portion 18 slidably disposed around the elongate portion 16. A part of the handle portion 11, for example, the spool portion 18, may be connected to a hypotube 22 which in turn may be connected to the control wires 14, 15. The elongate member 13 may having a coiled portion 153 covered by an outer jacket or a sheath 27 (see FIG. 14A). However, the elongate member 13 may not have a coiled portion 153, and instead may include a single layer tubular member. The end effector assembly 12 may be any type of assembly, for example, biopsy forceps jaws as depicted in FIG. 1. The control wires 14, 15 may be connected at their distal ends to opposing portions of the end effector assembly 12, and at their proximal ends to a hypotube 22. The hypotube 22 is connected to the spool portion 18. Longitudinal movement of the spool portion 18 relative to the elongate portion 16 causes the actuation of the end effector assembly 12 via the control wires 14, 15.

Figure 2:
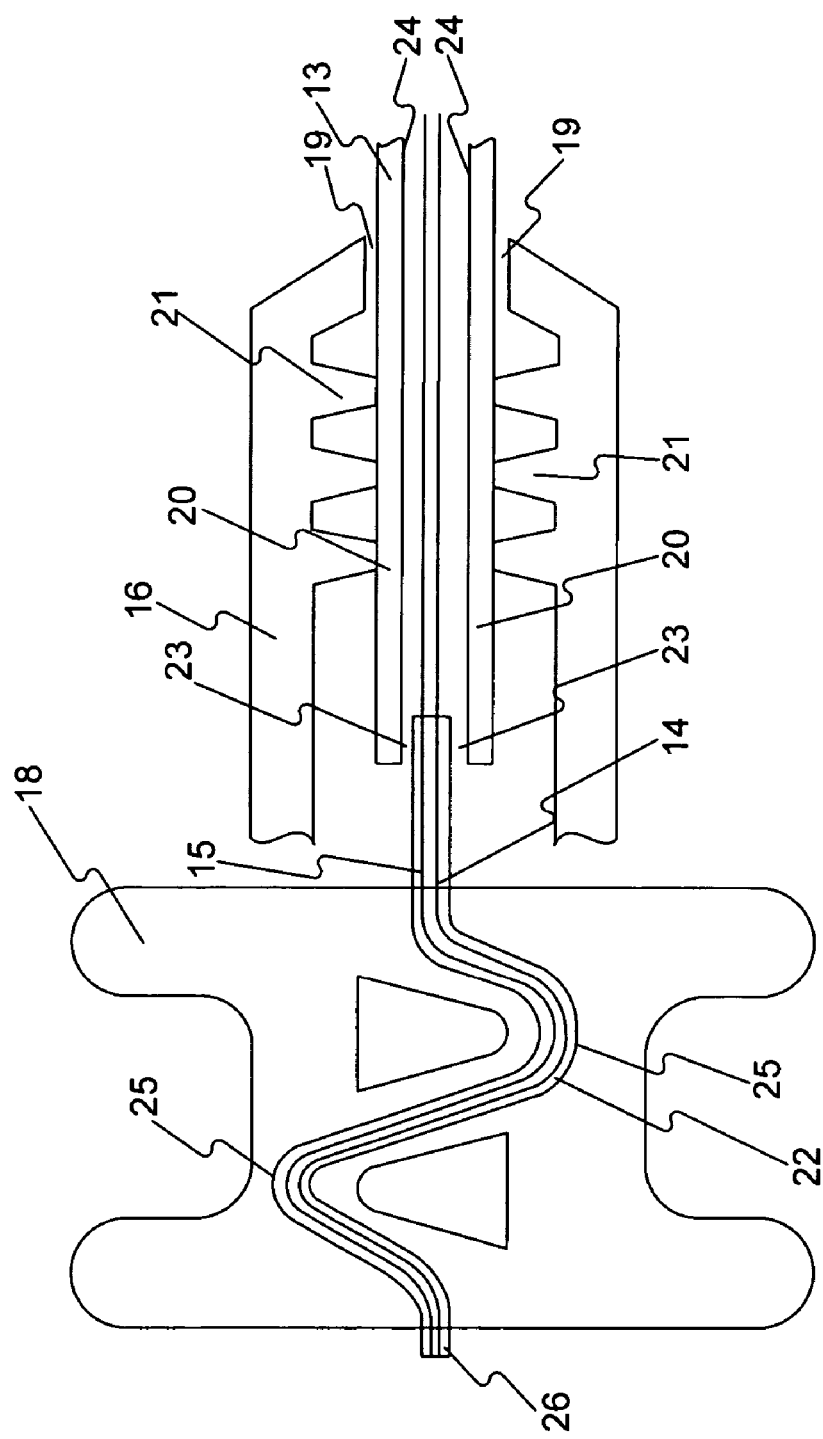
FIG. 2 is a cross-sectional schematic view of a proximal portion of an endoscopic instrument.

An interface between the elongate member 13, elongate portion 16, and spool portion 18 is depicted in FIG. 2. The elongate portion 16 includes a distal hole 19 which receives the proximal portion 20 of the elongate member 13. Rib portions 21 guide the proximal portion 20 of the elongate member 13 within the elongate portion 16, and may also fix the elongate member 13 within the elongate portion 16. The control wires 14, 15 extend through the elongate member 13 until they reach the proximal portion 20, and then enter the distal end of a hypotube 22. The hypotube 22, with the control wires 14, 15 therein, extends through the central cavity of the elongate portion 16 until they reach the spool portion 18. The hypotube 22 and control wires 14, 15 then extend through the spool portion 18, for example in roughly an S-type configuration, so as to secure the hypotube 22 and the control wires 14, 15 in the spool portion 18. The open proximal end 26 of the hypotube 22 may or may not extend through the proximal side of the spool portion 18.

The configuration shown in FIG. 2 includes certain leak paths permitting the passage of air, or other gas or liquid, from the lumen of the elongate member 13 to the external environment. For example, a gap 23 may exist between the elongate member 13 and the hypotube 22, for example, between the inner surface 24 of the elongate member 13 and the outer surface 25 of the hypotube 22. The gap 23 may be large enough to allow the passage of gas and/or fluid therethrough, for example, from the end effector assembly 12 via the lumen of elongate member 13 and to the external environment. Air or other gas or fluid also may pass through the open proximal end 26 of the hypotube 22 via the lumen of the elongate member 13 and hypotube 22.

Figure 3:
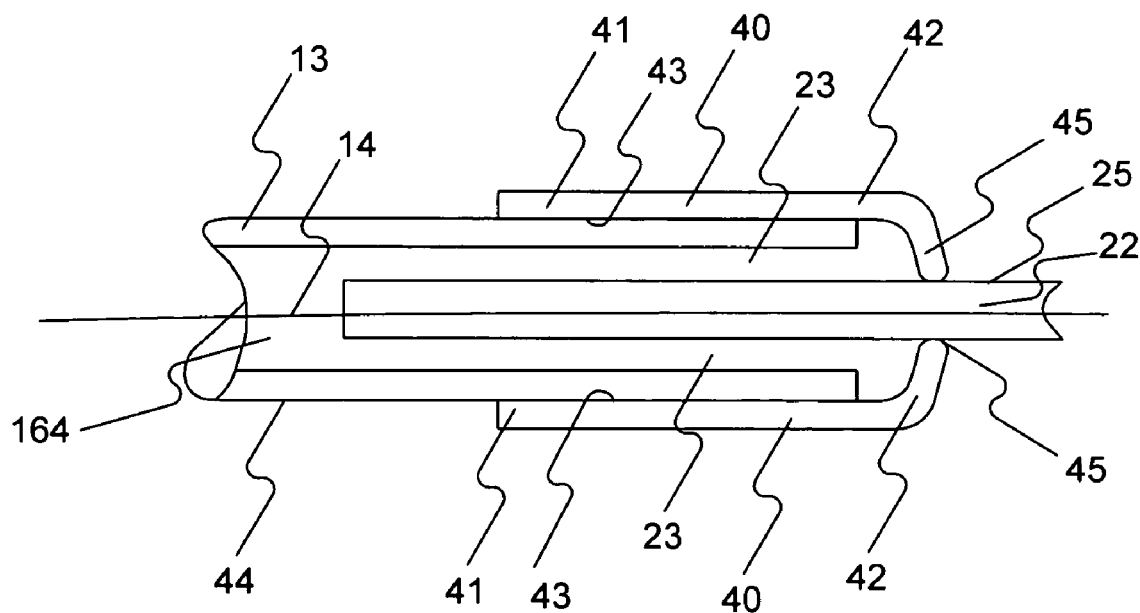
FIGS. 3 to 13 each is a schematic view of a sealing device of an embodiment of the present invention on an endoscopic instrument.

Embodiments of the present invention include seals to prevent the escape of air or other gas or fluid from a medical instrument. For example, FIG. 3 depicts an embodiment of a sealing device configured to prevent (or at least impede) fluid flow through gap 23. The sealing device 40 has a proximal portion 42 and a distal portion 41. The distal portion 41 is substantially cylindrical and has an inner diameter or circumference at surface 43 that is substantially the same as (or slightly less than) the outer diameter or circumference of elongate member at outer surface 44, so as to form a substantially fluid tight seal between the surfaces 43, 44. The proximal portion 42 has a substantially circular cross-section along its length, and tapers from the distal portion 41 until the end 45 of the proximal portion 41 contacts the outer surface 25 of the hypotube 22. The end 45 of the proximal portion 42 has substantially the same (or slightly less) diameter or circumference as the outer diameter or circumference of hypotube 22 at surface 25, so as to form a substantially fluid tight seal between end 45 of the proximal portion 42 and the outer surface 25 of the hypotube 22. Accordingly, the sealing device 40 assists in forming a substantially fluid tight seal between the elongate member 13 and the hypotube 22, such that no (or at least a reduced) amount of fluid flows into the central portion 164 of the handle elongate portion 16 from either the elongate member 13, the hypotube 22, or the gap 23 between the two.

The sealing device 40, and other sealing devices disclosed herein, may be formed of flexible silicone, rubber, plastic, or any other material suitable to substantially prevent (or at least impede) fluid from flowing across and/or permeating through it.

Figure 4:
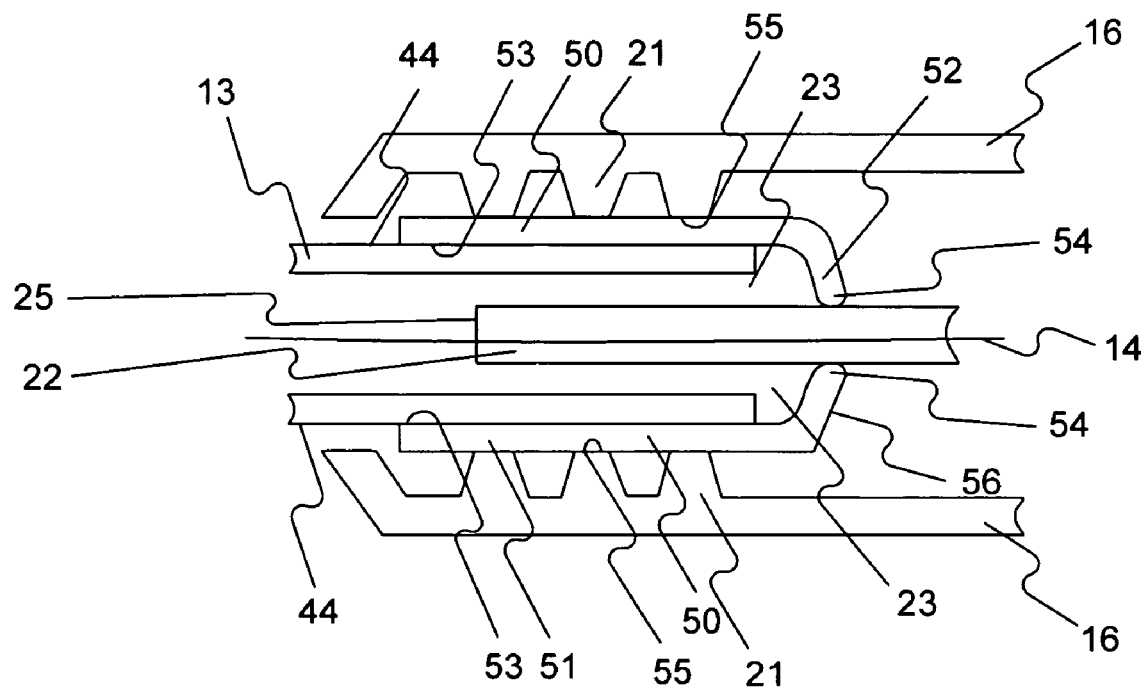

FIG. 4 depicts another exemplary embodiment of a sealing device configured to prevent (or at least impede) fluid flow through gap 23. The sealing device 50 has a distal portion 51 and a proximal portion 52 that are substantially similar to the distal portion 41 and proximal portion 42 of the sealing device 40 depicted in FIG. 3. In this embodiment, however, sealing device 50 is held in place between elongate portion 16 and elongate member 13.

More particularly, the inner surface 53 of the distal portion 51 and the outer surface 44 of the elongate member 13 are configured to form a substantially fluid tight seal, and the end 54 of the proximal portion 52 and the outer surface 25 of the hypotube 22 are also configured to form a substantially fluid tight seal. In this embodiment, the outer surface 56 of the sealing device 50 (at least along distal portion 51) interacts with the end portions 55 of the ribs 21 of the elongate portion 16 to assist in holding the sealing device 50 in place. For example, the sealing device 50 may be slightly compressed between the end portions 55 of the ribs 21 and outer surface 44 of the elongate member 13, so as to prevent longitudinal movement of the sealing device 50 relative to the elongate member 13 and/or the elongate portion 16.

Figure 5:
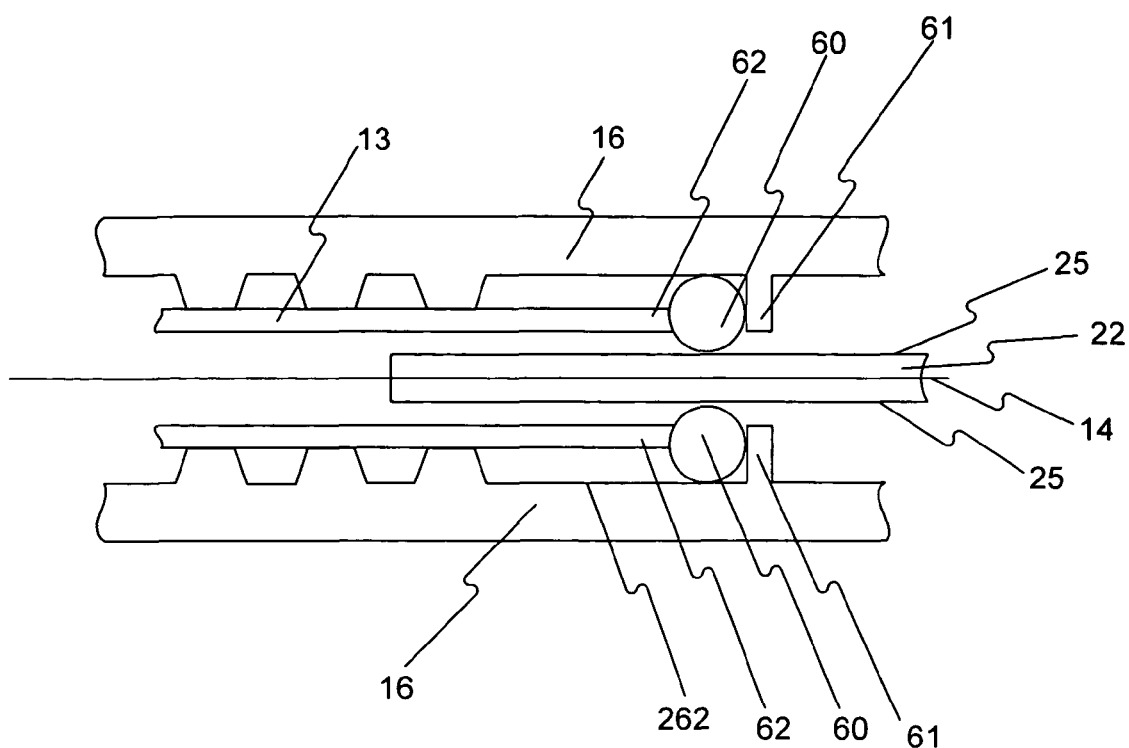

FIG. 5 depicts another exemplary embodiment of a sealing device configured to prevent (or at least impede) fluid flow through gap 23. The sealing device is substantially an O-ring 60 disposed between the proximal end 62 of the elongate member 13, the outer surface 25 of the hypotube 22, and an inner protrusion 61 of the elongate portion 16. The inner diameter or circumference of the O-ring 60 is substantially the same as (or slightly less than) the outer diameter or circumference of hypotube 22 at surface 25, such that a substantially fluid tight seal is formed between the O-ring 60 and hypotube 22. The O-ring 60 also, at least when compressed between the proximal end 62 of the elongate member 13 and the inner protrusion 61 of the elongate portion 16, forms a substantially fluid tight seal between the O-ring 60 and the elongate member 13. However, the O-ring 60 may also form a substantially fluid tight seal with the proximal end 62 of the elongate member 13 irrespective of whether the O-ring 60 is contacting the inner protrusion 61. A seal may also be formed between the O-ring 60 and the inner surface 262 of the elongate portion 16.

As an alternative to using inner protrusion 61 to anchor O-ring 60 against elongate member 13, O-ring 60 may be affixed or otherwise coupled to member 13 in any suitable manner, such as an adhesive.

Figure 6:
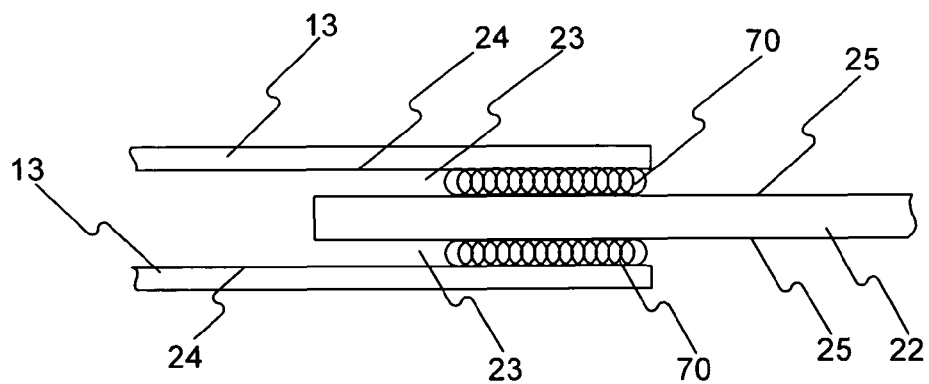

FIG. 6 depicts still another exemplary embodiment of a sealing device configured to prevent (or at least impede) fluid flow through gap 23. Grease 70, or any other viscous substance, may be placed in at least a portion of gap 23 between the inner surface 24 of the elongate member 13 and the outer surface 25 of the hypotube 22. The grease 70 may prevent air or fluid from escaping the elongate member 13 through the gap 23. The grease 70 also allows the sealing of the gap 23 despite any potential movement of the hypotube 22 relative to the elongate member 13, as the grease 70 may be placed along a sufficient portion of the gap 23 so that despite movement of the hypotube 22 relative to the elongate member 13, some grease 70 will still remain in the gap 23.

Figure 7:
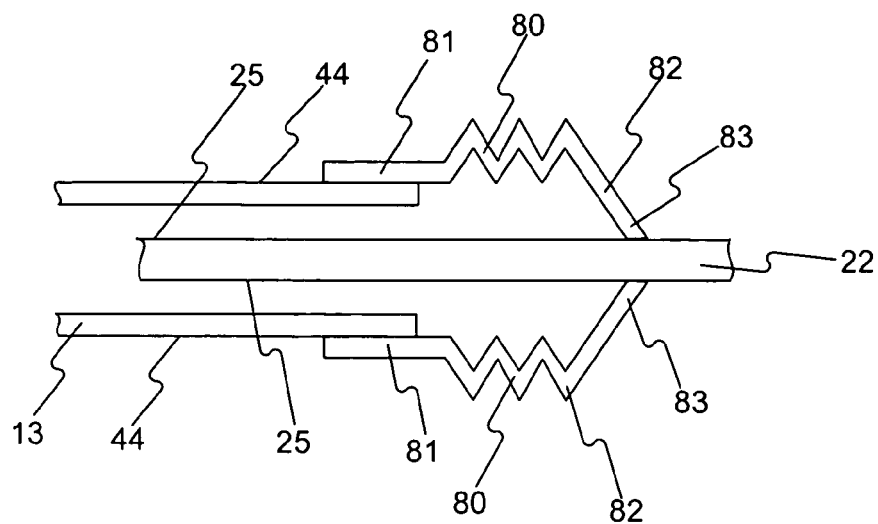

FIG. 7 depicts a further exemplary embodiment of a sealing device configured to prevent (or at least impede) fluid flow through gap 23. The sealing device 80 includes a distal portion 81 substantially similar to the distal portions 41, 51 set forth above in connection with FIGS. 3 and 4. The sealing device 80 also has a bellows portion 82 with an end portion 83 that is substantially similar to the end portions 45, 54 described above in connection with FIGS. 3 and 4. The bellows portion 82 is configured to connect the distal portion 81 and the end portion 83, and also to allow movement of the hypotube 22 relative to the elongate member 13, in that the bellows portion 82 will collapse and expand to adapt to longitudinal movement of the hypotube 22 and elongate member 13 relative to each other. This allows the distal portion 81 and the end portion 83 to be more securely fastened and/or sealed relative to the elongate member 13 and the hypotube 22, respectively, as the distal portion 81 and the end portion 83 do not need to move relative to surfaces 44, 25.

In various embodiments, for example of the sealing devices in FIGS. 3 and 4, the inner surface of the distal portion and the outer surface of the elongate member may slightly interfere with each other such that a seal is formed between the surfaces. However, the inner surface of the distal portion may also have a circumference or diameter larger than the circumference or diameter of the outer surface of the elongate member. While in such a state a completely fluid tight seal may not necessarily be formed, such a configuration is sufficient to substantially impede fluid flow. The end of the proximal portion and the outer surface of the hypotube may also slightly interfere with each other such that a seal is formed between the end and the surface. However, the end of the proximal portion may also have a circumference or diameter slightly larger than that of the outer surface of the elongate member. While in such a state a completely fluid tight seal may not necessarily be formed, such a configuration is sufficient to substantially impede fluid flow. The sealing devices may move longitudinally relative to the elongate member and/or hypotube and still maintain the substantially fluid tight sealed state.

In various embodiments, the inner surface of the hypotube may surround the outer surface of the elongate member, and thus there may be a gap between the outer surface of the elongate member and the inner surface of the hypotube through which gas or fluid may flow. Accordingly, at least certain features of the embodiments set forth above may be reversed. For example, grease may be applied to the outer surface of the elongate member and inner surface of the hypotube. In another example, the proximal portion of the sealing device in FIGS. 3, 4, and 7 may be substantially cylindrical, and the distal portion may taper into an end that seals against the elongate member. In yet another example, the O-ring may be placed around the outer surface of the elongate member and abut an end of the inner surface of the hypotube. Other variations will be apparent to those of ordinary skill in the art.

Figure 8:
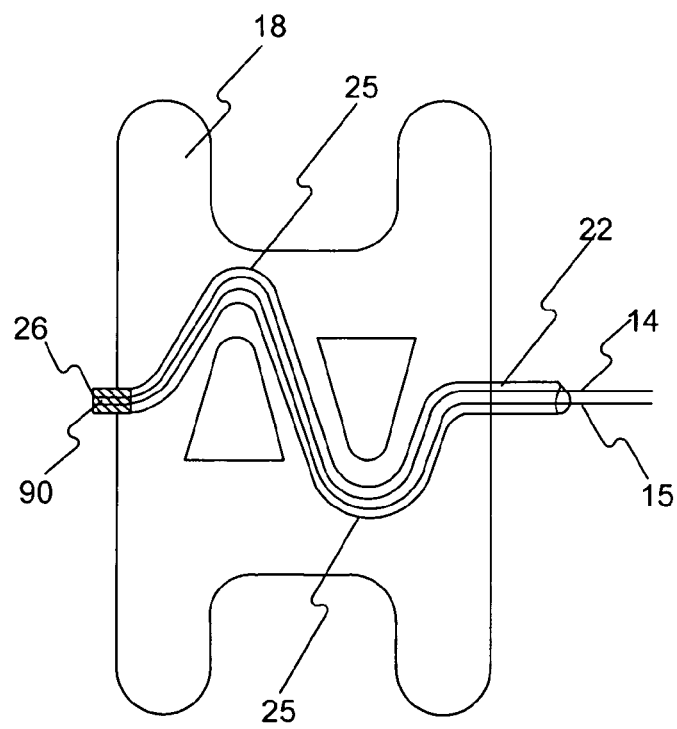

FIG. 8 depicts an exemplary embodiment of a sealing device configured to prevent (or at least impede) fluid flow through the open proximal end 26 of hypotube 22. The sealing device 90 is solder or other suitable material, for example adhesives, disposed in the proximal end 26 of the hypotube 22. The sealing device 90 fills substantially the entire proximal end 26 and is configured to resist pressure, for example from the interior of the hypotube 22, in order to prevent fluid flow therethrough. The sealing device 90 may also secure the control wires 14, 15 in the hypotube 22 and/or prevent their movement longitudinally relative to the hypotube 22.

Figure 9:
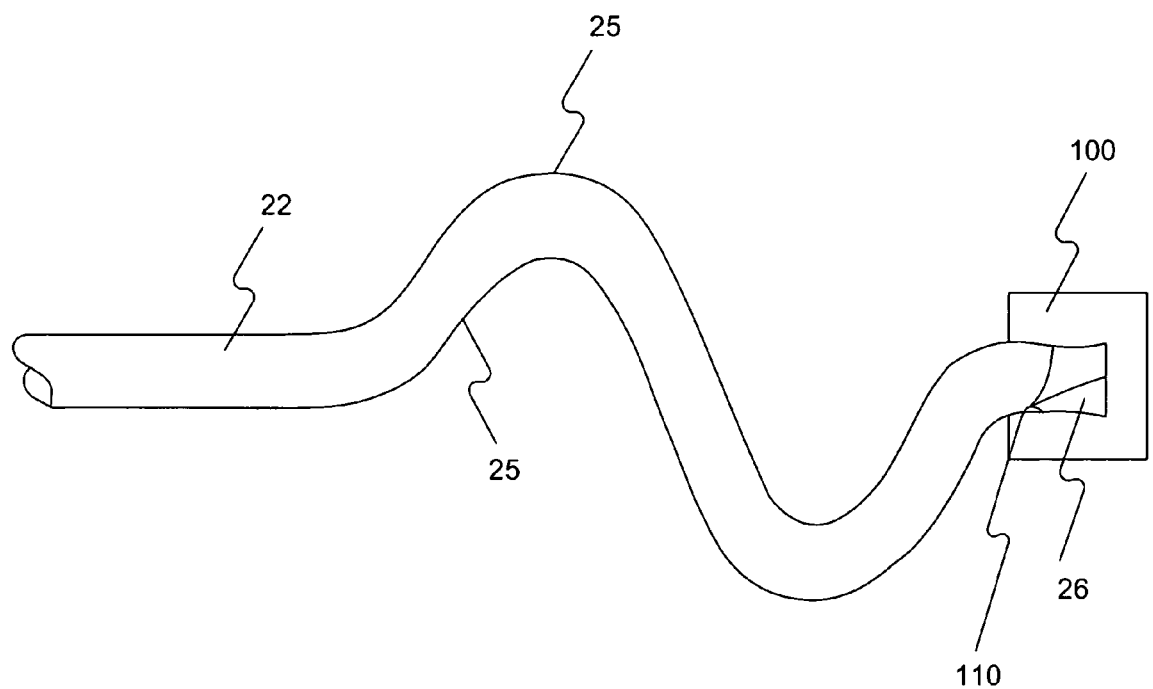

FIG. 9 depicts another exemplary embodiment of a sealing device configured to prevent (or at least impede) fluid flow through the open proximal end 26 of hypotube 22. The sealing device is a cap 100 that is securely fastened around the proximal end 26 of the hypotube 22. The inner surface 101 of the cap 100 and the outer surface 25 of the hypotube 22 form a substantially fluid tight seal. The cap 100 and hypotube 22 may fit snugly through a friction fit or other suitable coupling means, such as adhesive.

Figure 10:
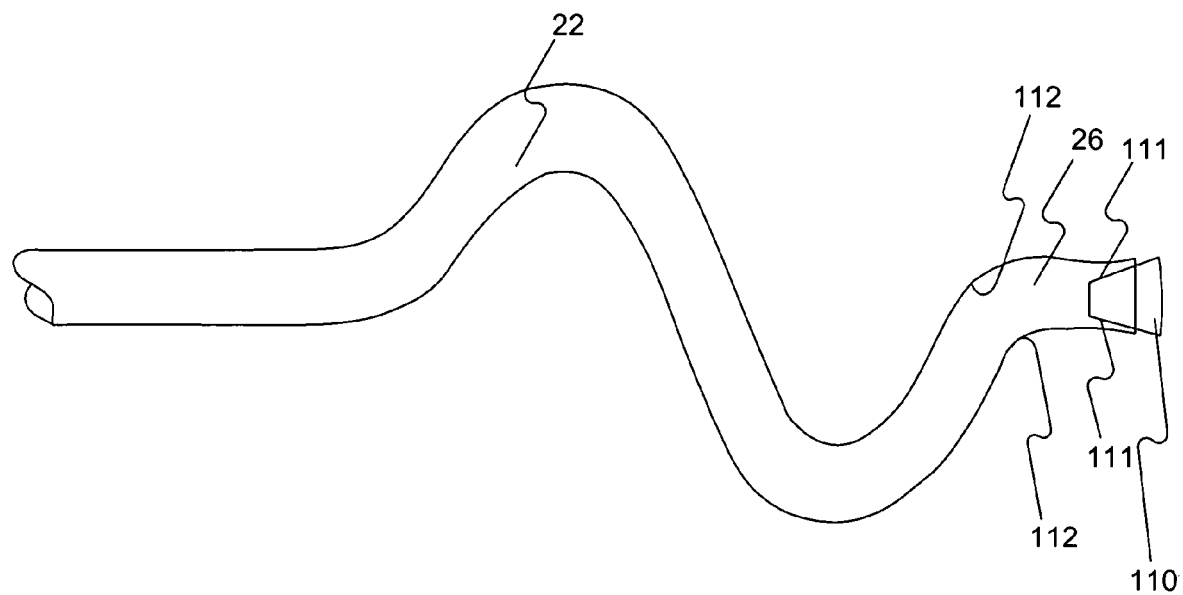

FIG. 10 depicts still another exemplary embodiment of a sealing device configured to prevent (or at least impede) fluid flow through the open proximal end 26 of hypotube 22. The sealing device is a plug 110 that is securely disposed in the proximal end 26 of the hypotube 22. The outer surface 111 of the plug 110 has a substantially circular cross-section along its entire length, and tapers from its proximal end to its distal end. The outer surface 111 is inserted into the proximal end 26 of the hypotube 22 until it forms a substantially fluid tight press fit with the inner surface 112 of the hypotube 22. In such a configuration, at least some of the plug 110 may be disposed in the hypotube 22. In other embodiments, the plug may be non-tapered and/or substantially the entire plug may be configured to fit inside the hypotube 22.

Figure 11:
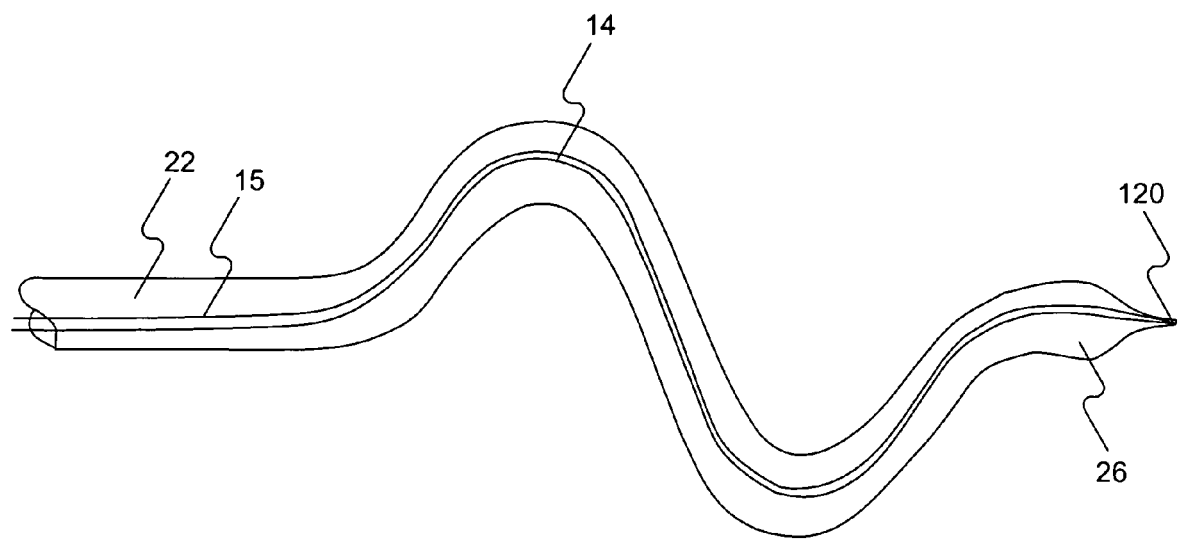

FIG. 11 depicts yet another exemplary embodiment of a sealing device configured to prevent (or at least impede) fluid flow through the open proximal end 26 of hypotube 22. The hypotube 22 has a crimped portion 120 at its proximal end 26 configured to prevent fluid flow therethrough. The crimped portion 120 may also secure the control wires 14, 15 in the hypotube 22 so as to substantially prevent longitudinal movement of the control wires 14 relative to the hypotube 22. The crimped portion 120 may be formed by any method known in the art.

Figure 12:
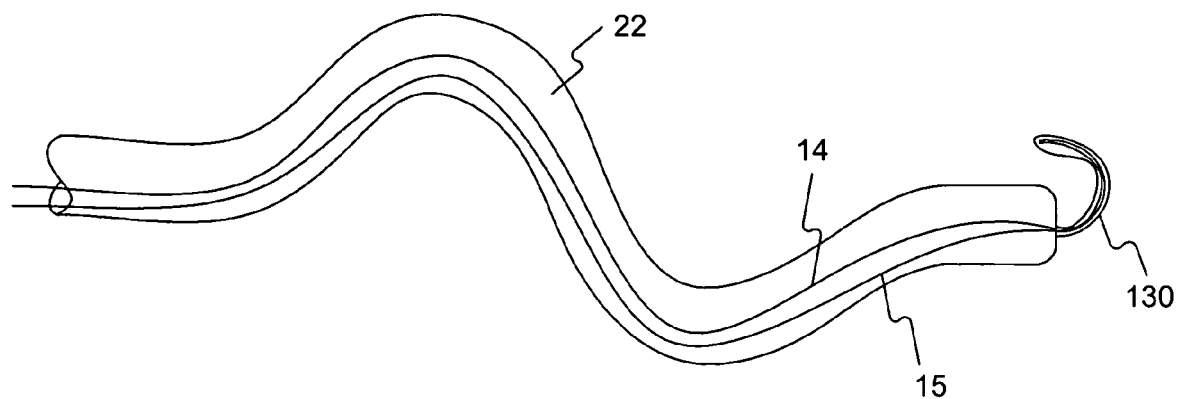

FIG. 12 depicts yet another exemplary embodiment of a sealing device configured to prevent (or at least impede) fluid flow through the open proximal end 26 of hypotube 22. Here, the hypotube 22 has a crimped portion 130 substantially similar to the crimped portion 120 in FIG. 11, except that the crimped portion 130 is folded over, for example, to assist in keeping the crimped portion 130 from unraveling and/or to provide a tighter seal. The control wires 14, 15 may be secured in crimped portion 130 in substantially the same manner as set forth above in FIG. 11, or the control wires 14, 15 may fall short and not be disposed in the crimped portion 130 at all.

Figure 13:
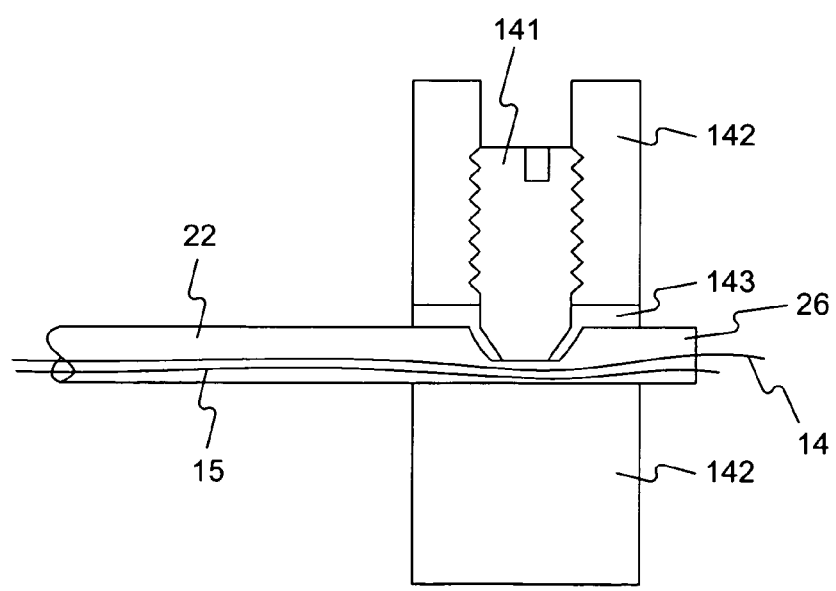

FIG. 13 depicts a still further exemplary embodiment of a sealing device configured to prevent (or at least impede) fluid flow through the open proximal end 26 of hypotube 22. The sealing device includes a set screw assembly 140. The set screw assembly 140 has a set screw 141 secured in a housing 142 configured to receive and retain the set screw 141. The housing 142 also has a passage 143 through which the hypotube 22 can be passed through. Once the proximal end 26 of the hypotube 22 is in or extended past the passage 143, the set screw 141 in the housing 142 is screwed onto the hypotube 22 so as to deform the hypotube 22 so that fluid cannot flow therethrough. The control wires 14, 15 also may be held in the hypotube 22 by the set screw assembly 141 in the same manner as the hypotube 22 is held in the passage 143, so that the control wires 14, 15 are substantially prevented from shifting longitudinally relative to the hypotube 22.

Figure 14A:
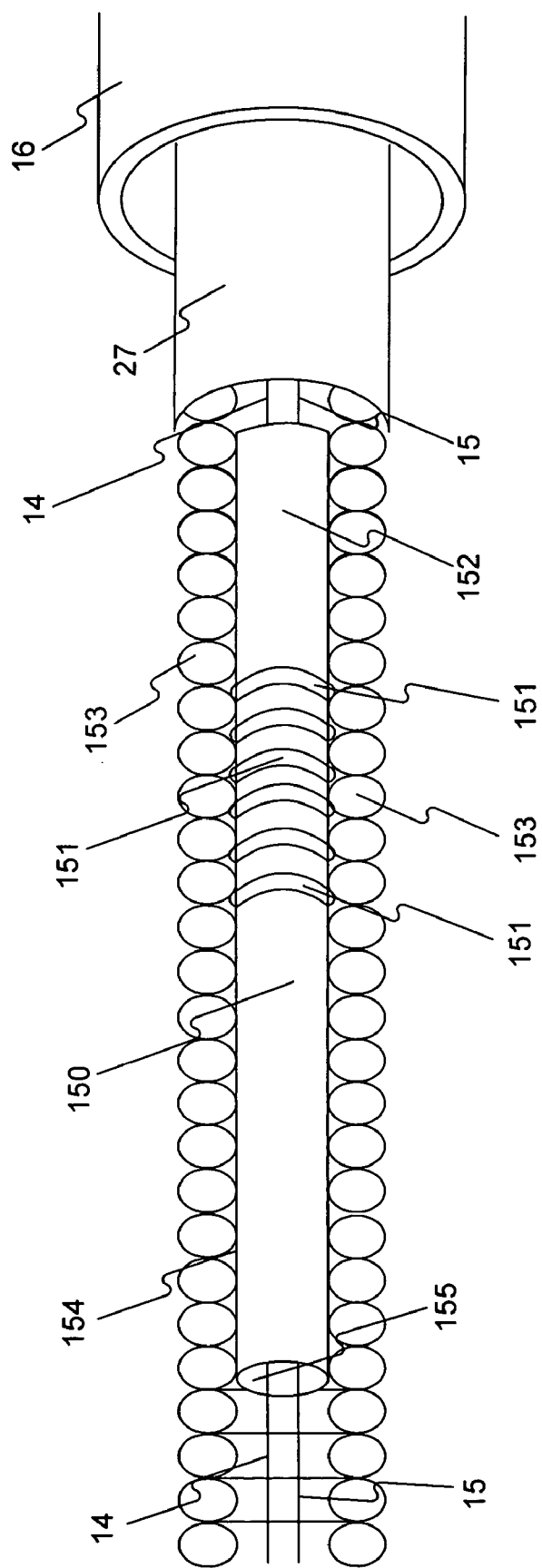
FIG. 14A is a schematic view of a sealing device of another embodiment of the present invention on the endoscopic instrument.
Figure 14B:
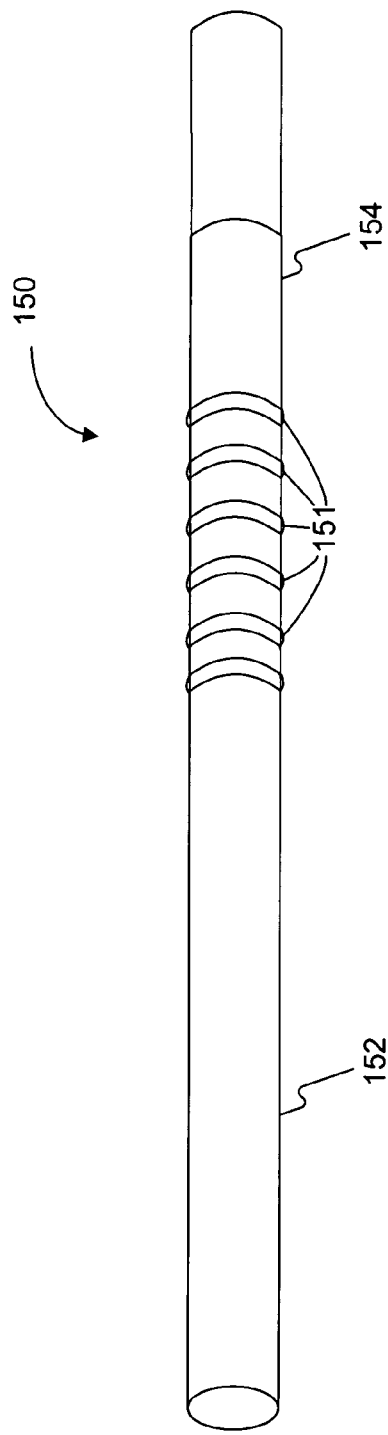
FIG. 14B is a schematic view of the sealing device of FIG. 14A.
Figure 14C:
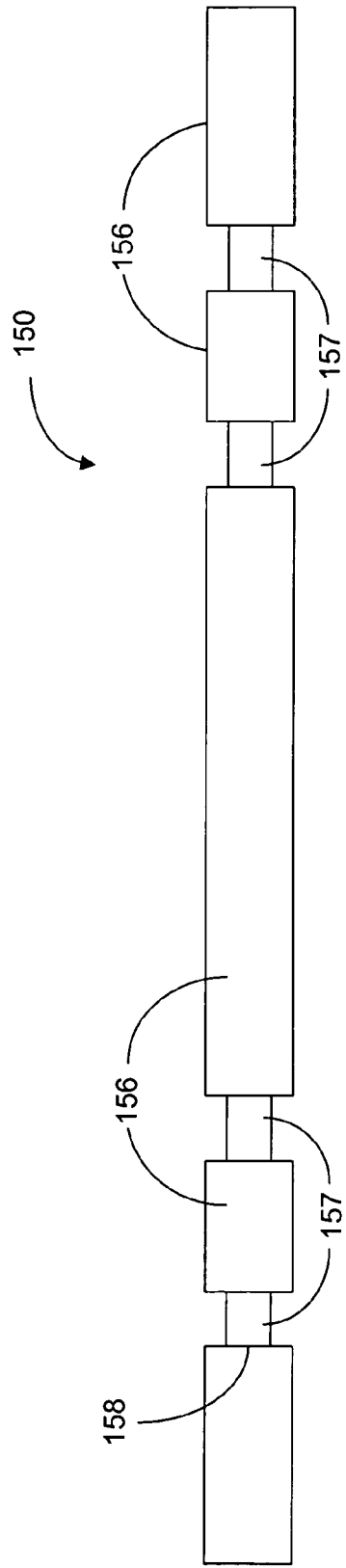
FIG. 14C is an internal view of the sealing device of FIG. 14A.

FIGS. 14A-14C depict an exemplary embodiment of a sealing device configured to prevent (or at least impede) fluid flow through the elongate member 13. The sealing device is a plug 150. The plug 150 has a plurality of external threads 151 extending radially outward from its central tube 152. The external threads 151 are configured, for example, to screw into the coiled section 153 of the elongate member 13 and engage the depressions in the coiled section 153, i.e. the spaces between adjacent coils of the elongate member 13. However, the external threads 151 of the plug 150 also may be flexible enough such that the plug 150 can be advanced into the hollow portion of the elongate member 13 without screwing or threading. In such a case, during advancement of the plug 150, the external threads 151 will bend and, once positioned, will expand between coils in the coiled section 153. A substantially fluid tight seal is formed between at least a portion of the outer surface 154 of the plug 150, especially the portion that includes the external threads 151, and the inner surface 155 of the coiled section 153.

The interior of the plug 150, as depicted in FIG. 14C, has a plurality of chambers 156 with connecting passages 157. The connecting passages 157 have a smaller cross-sectional area than the chambers 156. The connecting passages 157 are configured such that the control wires 14, 15 may pass through them, for example, because the connection passages have a cross-sectional area slightly larger than the combined cross-sectional areas of the control wires 14, 15. The chambers 156 and the connecting passages 157 are also configured not to substantially impede the longitudinal movement of the control wires 14, 15 relative to the plug 150 or the elongate member 13. The chambers 156 and connecting passages 157 are configured to impede and/or prevent fluid flow through the interior of the plug 150. For example, air or other fluid that enters the distal most chamber 156 will contact the proximal wall 158 of the chamber 156 and attempt to pass through more proximal connecting passages 157 and chambers 156. Accordingly, as the gas or fluid reaches the proximal end of the plug 150, it will have lost substantially velocity, pressure, and/or momentum it had when entering the distal end of the plug 150. In another example, fluid attempting to enter the proximal end of the plug 150 and exit the distal end of the plug 150 will encounter substantially the same effect.

In various embodiments, the sealing devices need not form a completely fluid tight seal, or even any seal at all, between the components of the endoscopic instrument. Indeed, the sealing devices may simply impede the flow of fluid therethrough, for example, to reduce the velocity, pressure, and/or volume of fluid flowing through the endoscopic instrument.

In various embodiments, any of the sealing devices may be used on other portions of the endoscopic instrument, including other portions of the handle, elongate member, and distal end effector assembly, as appropriate. In various embodiments, different combinations of any of the above sealing devices may be used. For example, an endoscopic instrument may have both a plug 150 within elongate member 13 and grease 70 in the gap 23. In other example, the proximal end 26 of the hypotube 22 may have both solder 90 and a cap 100. Accordingly, any combination of the above sealing devices is contemplated. The invention may be used in conjunction with any medical or non-medical device and with any medical or non-medical procedure.

Embodiments of the invention also include methods of advancing fluid through portions of elongate devices. Fluids that may be advanced through portions of elongate devices include cleaning fluids, sterilizing fluids, saline solution, water, viscous substances, oils, lubrication, disinfecting fluids, drugs or other medications, visual contrast dyes, X-ray contrast dyes, and any other fluid known in the art. For example, to clean an endoscopic instrument, it may be desirable to pass fluid through the instrument, including a lumen of the elongate member for example. One method includes plugging the end effector assembly into a vacuum receptacle and submerging the handle portion into a tank of fluid. A vacuum is then pulled on the receptacle and the tank is pressurized. As a result, fluid is forced and/or advanced into the end effector assembly from the handle portion via the lumen of the elongate member. Ultrasound vibrations and/or heat may be used to assist in the cleaning of the endoscopic instrument. In endoscopic devices that include seals according to any of the embodiments of the invention, including those described above, however, the seal may hinder the passage of the fluid. Thus, other methods of passing fluid through the endoscopic device to, for example, clean the device, are required.

In an exemplary embodiment of the method of the present invention, an endoscopic instrument having a sealing device, for example one of the sealing devices set forth above, is provided. Before advancing fluid through the endoscopic instrument, the sealing device may be removed, for example, by disassembling at least that portion of the endoscopic instrument accommodating the sealing device. The endoscopic instrument, without the sealing device, may then have fluid advanced through it using any method known in the art, for example using the method set forth above, and then the endoscopic instrument may be reassembled. After advancing fluid through the endoscopic instrument, the sealing device may or may not be placed back on or within the endoscopic instrument.

Figure 15A:
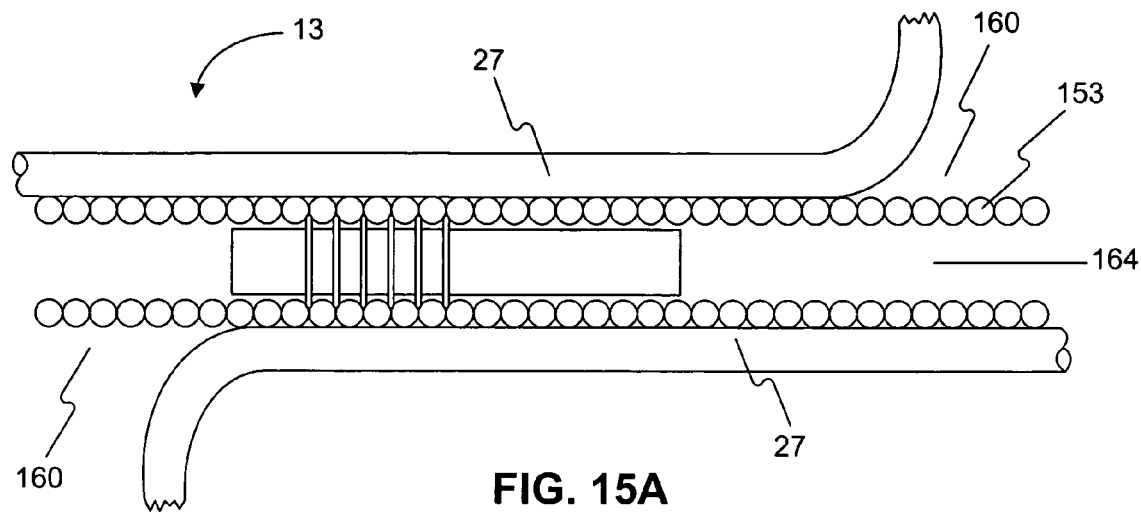
FIGS. 15A to 18 each is a schematic view of a method of advancing fluid through a lumen of a medical instrument according to an embodiment of the present invention.
Figure 15B:
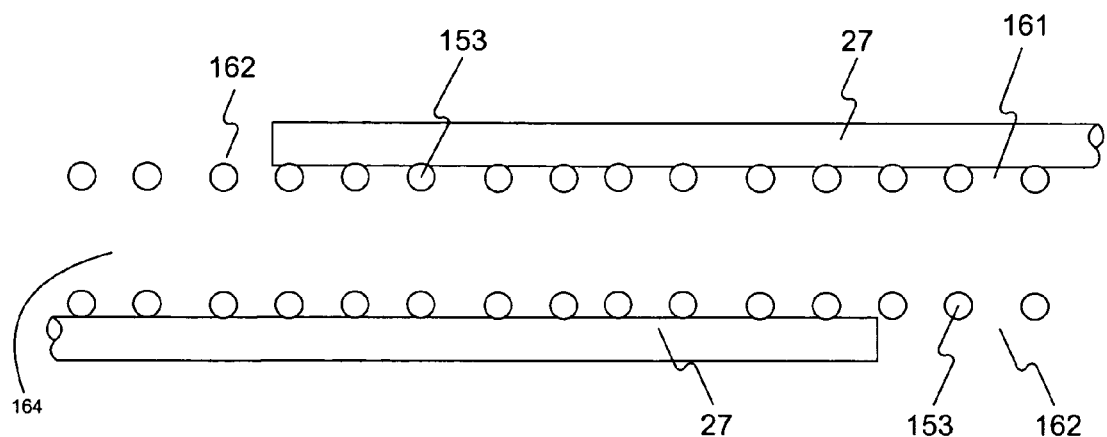

As depicted in FIG. 15A, in another exemplary embodiment of the method of the present invention, an endoscopic instrument having a sealing device, for example one of the sealing devices set forth above, is provided. An outer covering or jacket 27 on the elongate member 13 is at least partially peeled back from coiled section 153 of the elongate member 13. Fluid may then be advanced through the endoscopic instrument 10, for example through the peeled, uncovered portions 160 of the coiled section 153, and into the lumen of the elongate member to the handle 11 and/or the end effector assembly 12. By removing the outer covering or jacket 27, the fluid may bypass the sealing devices. Fluid may be injected into the elongate member lumen between adjacent coils through any suitable method, including methods described below. If the coiled section 153 is placed under tension by, for example pulling or bending the coiled section, gaps 161 form between adjacent coils of the coiled section 153, such as the gaps shown in FIG. 15B. These gaps 161 may assist in the delivery of fluid to the lumen of elongate member 13. After delivery of fluid, jacket 27 may or may not be replaced, as desired.

Figure 15C:
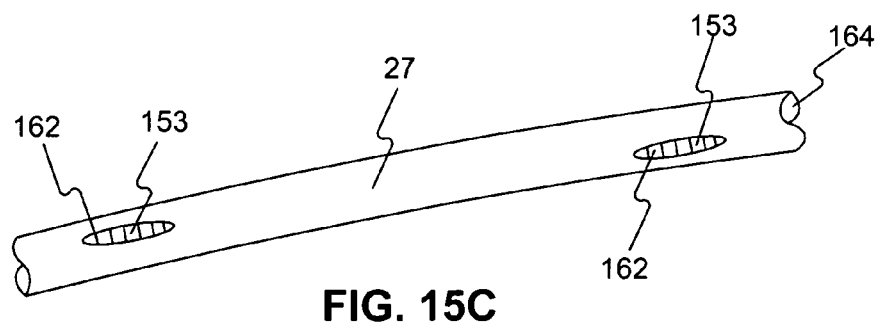

In other embodiments, for example as shown in FIG. 15C, the outer covering or jacket 27 may not be removed, but have slits 162 cut therein so as to allow fluid to flow through the coils of the coiled section 153, through any suitable injection method, into the lumen 164 of the elongate member 13. The slits 162 may be cut in portions of the outer covering or jacket 27 on both or either side of the sealing device and/or devices so as to facilitate fluid flow around the sealing device and/or devices. The fluid may then advance through the elongate member lumen and to the handle 11, the end effector assembly 12, and/or other portions of the endoscopic instrument 10. After advancing the fluid, the outer covering 27 or jacket 27 may either be placed back on the coiled sections 153 of the elongate member 13 or may be repaired such that fluid no longer enters the central hollow portion (lumen) 164 of the elongate member 13 through the coiled section 153, or may be left off the endoscopic instrument 10.

In a further embodiment of the method of the present invention, an endoscopic instrument having a sealing device, for example one of the sealing devices set forth above, is provided. A needle containing a fluid is then used to place the fluid into the device. From there, the fluid may flow through the elongate member, the handle, the end effector assembly, the sealing device, and/or any other portion of the endoscopic instrument.

Figure 16:
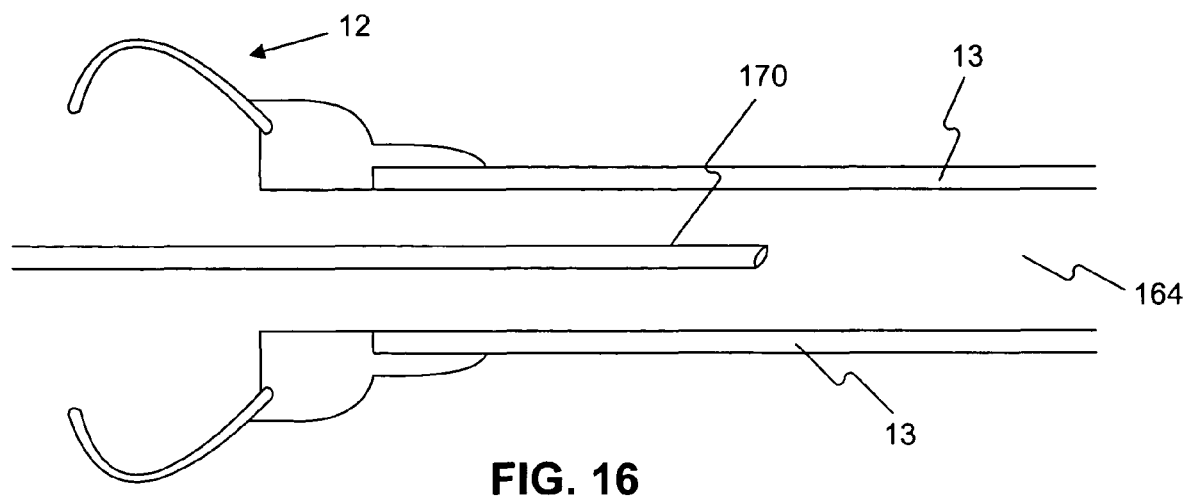

For example, as shown in FIG. 16, a long injection needle 170 may be placed into the end effector assembly 12 and/or a part of the hollow central portion 164 of the elongate member 13. The fluid is then injected into that portion of the endoscopic instrument, and the fluid may then flow proximally from there until it reaches the distal end of the sealing device. The fluid may also flow distally from there until it reaches the proximal end of the elongate member 13 and/or the end effector assembly 12. The needle 170 may also be used to remove the fluid from portions of the endoscopic instrument, for example, the fluid that it or another needle injected into the endoscopic instrument. The needle 170 may be removed after its use.

Figure 17:
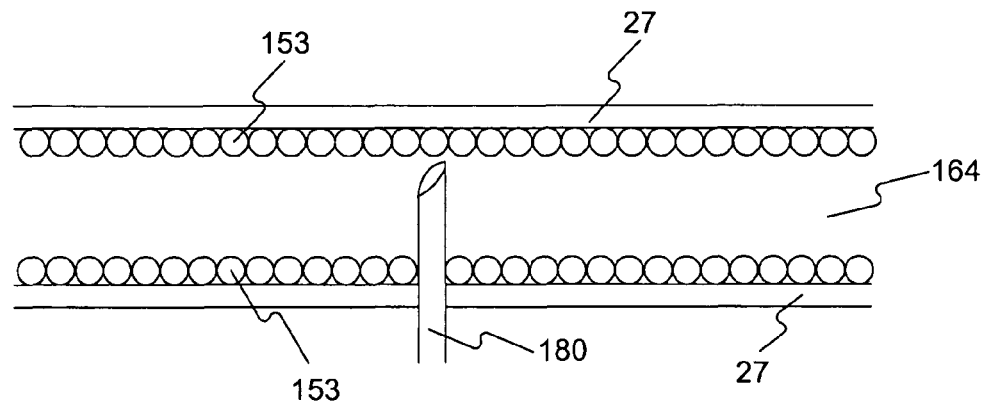

In another example, as shown in FIG. 17, a hypodermic needle 180 may be used to pierce the elongate member 13, for example the outer covering and/or jacket 27 and/or a coiled portion 153, and the fluid may be injected into the hollow lumen 164 of the elongate member 13. Depending on where the fluid is injected in the elongate member 13, for example proximal to or distal to the sealing device, the fluid may flow toward the handle 11, the sealing device, the elongate member 13, and/or the end effector assembly 12.

In yet another example, the hypodermic needle 180 could pierce a portion of the handle 11, (e.g., the elongate portion 16, the spool portion 18, and/or the hypotube 22) and the fluid could then be injected into that handle portion 11. Depending on where the fluid is injected in the handle portion 11, for example proximal to or distal to the sealing device, the fluid may flow to other portions of the handle 11, the sealing device, the elongate member 13, and/or the end effector assembly 12.

Figure 18:
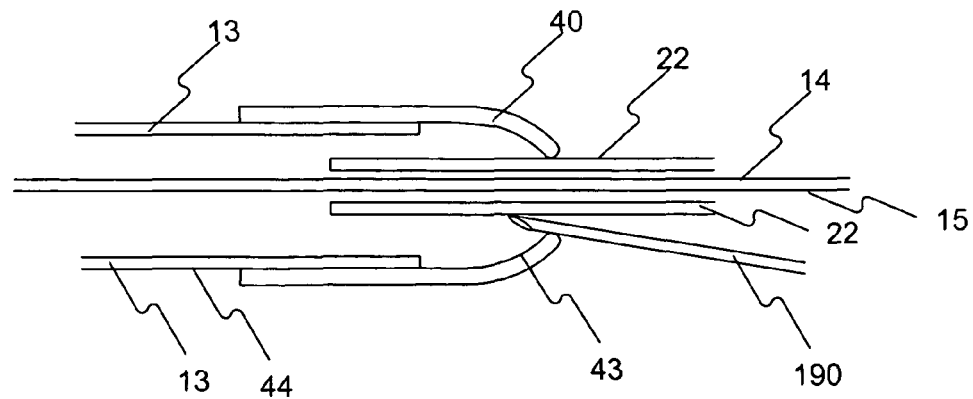

In still another example, as shown in FIG. 18, a needle 190 could be used to force fluid around the sealing device, for example the sealing device 40 of FIG. 3. The needle 190, however, may be used with any sealing device of the present invention. A needle 190 may be advanced to the sealing device 40 from any direction, and then the distal end of the needle 190 could be advanced between the inner surface 43 of the sealing device 40 and the outer surface 44 of the elongate member 13. Once past the region where the sealing device 40 and the elongate member 13 meet, fluid could be injected into the elongate member 13 on the side of the sealing device 40 opposite the rest of the needle 190, and then fluid could flow to the elongate member 13, the end effector assembly 12, and/or the handle 11. In a variation of the previous example, the needle 190 could also be forced through, as opposed to around, the sealing device 40. After interaction with the needle 190, the sealing devices 40 may need to be repaired and/or repositioned in the endoscopic instrument 10.

In a still further embodiment of the method of the present invention, an endoscopic instrument having a sealing device, for example one of the sealing devices set forth above, is provided. The sealing device may then be partially removed and/or dislodged from the endoscopic instrument so as to allow fluid flow through the previously sealed portion. The partial removal and/or dislodging of the sealing device may be accomplished, for example, by advancing a pin, tweezers, and/or other like device, into the sealed portion of the endoscopic instrument and then manipulating the sealing device with the pin, tweezers, or device. Once fluid has been advanced through the endoscopic instrument, including the previously sealed portion, the sealing device may either be reconfigured such that it once again prevents fluid flow through that portion of the endoscopic instrument, for example using the aforementioned pin, tweezers, or device, or it may be left as is so as to permit fluid flow therethrough.

In still another embodiment of the method of the present invention, an endoscopic instrument having a sealing device, for example one of the sealing devices set forth above, is provided. At least a portion of the endoscopic instrument is submerged in fluid inside of a sealed chamber. A vacuum may then be used on the sealed chamber to draw at least some of the air from the interior of the endoscopic instrument, including the interior portions adjacent to the sealing device. The chamber then may be pressurized so as to force fluid into the interior of the endoscopic instrument, for example, the interior portions of the endoscopic instrument adjacent to the sealing device from which air was evacuated. The fluid may then be removed from the interior portions of the endoscopic instrument, for example, by using a vacuum, injecting air into the interior portions, utilizing gravity, or using other forces.

In another embodiment of the method of the present invention, an endoscopic instrument having a sealing device, for example one of the sealing devices set forth above, is provided. A portion of the endoscopic instrument is connected to a pressurized fluid device, for example a device which expels gas or fluids at high pressure, such that the pressurized fluid device is in flow communication with the sealing device. The pressurized fluid device may then be used to force a gas or fluid through the endoscopic instrument at sufficiently high pressure to "blow out" and/or damage the sealing device. After the sealing device has been blown out or damaged, the endoscopic instrument may be connected to a fluid device which expels gas or fluids at lower pressure. This fluid device may be used to advance fluid through the now unsealed endoscopic instrument. After advancing the fluid, the sealing device may be reconstituted on or within the endoscopic instrument, or it may be left off and/or in its damaged state.

In various embodiments, any of the above methods of the present invention may be repeated to achieve the desired effect and/or result. In addition, any of the above methods may be used with any of the other methods so as to achieve the desired effect and/or result. For example, once a sealing device is removed from the endoscopic instrument and fluid has been advanced through the endoscopic instrument, another sealing device may be placed on the endoscopic instrument. The other sealing device may be of the same type as the previously removed sealing device, or it may be of a different type.

In various embodiments, the methods described above are used to advance fluid through the sealed medical instrument by bypassing the sealing device. Bypassing may also include advancing fluid up to the sealing device without necessarily flowing fluid past the sealing device.

In various embodiments, all aspects of the invention set forth herein may be used in conjunction with any medical device, instrument, or procedure, and/or any non-medical device, instrument, or procedure. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A medical device comprising:
   a handle portion;
   an end effector assembly;
   an elongate member connecting the handle portion to the end effector assembly; and
   a sealing device associated with at least one of the handle portion and the elongate member to substantially prevent flow communication between a lumen of the elongate member and an environment external to the device;
   wherein a distal-most end of the sealing device which is closest to the end effector assembly has a radially inner surface disposed radially outward of a radially outer surface of the elongate member,
   wherein the distal-most end of the sealing device comprises at least one of a silicone, a rubber, and a plastic,
   wherein the handle portion includes protrusions contacting the sealing device, and
   wherein the handle portion includes a tube in flow communication with the elongate member.

2. The device of claim 1, wherein the sealing device is configured to substantially prevent fluid flow through a gap between the tube and the elongate member.

3. The device of claim 2, wherein the sealing device is disposed around the elongate member and the tube.

4. The device of claim 2, wherein the sealing device is configured to form a substantially fluid tight seal with the elongate member.

5. The device of claim 2, wherein the sealing device is configured to form a substantially fluid tight seal with the tube.

6. The device of claim 2, wherein the sealing device is configured to form a substantially fluid tight seal between the elongate member and the tube.

7. The device of claim 3, wherein the sealing device is configured to allow longitudinal movement of the tube relative to the elongate member.

8. The device of claim 3, wherein a tip of the sealing device is configured to form a substantially fluid tight seal with the tube.

9. The device of claim 1, wherein the sealing device is disposed between an inner surface of the handle portion and an outer surface of the elongate member.

10. The device of claim 1, wherein the sealing device is configured to form a substantially fluid tight seal between the sealing device and a proximal end of the elongate member.

11. The device of claim 1, wherein the sealing device is an elastic sleeve.

12. The device of claim 1, wherein the tube is configured to be in flow communication with the environment external to the device via a proximal end of the tube.

13. The device of claim 12, wherein the sealing device is disposed on the tube.

14. The device of claim 12, wherein the sealing device is a cap at the proximal end of the tube.

15. The device of claim 1, wherein a portion of the sealing device which extends over the elongate member has a length, and an outer diameter of the sealing device along the length is substantially constant.

16. The device of claim 1, wherein a proximal end of the sealing device has a first outer diameter and a distal end of the sealing device has a second outer diameter, and
   wherein the first outer diameter is smaller than the second outer diameter.

17. The device of claim 1, wherein a portion of the sealing device which extends over the elongate member consists essentially of at least one of a silicone, a rubber, and a plastic.

18. A medical device comprising:
   a handle portion;
   an end effector assembly;
   an elongate member connecting the handle portion to the end effector assembly; and
   a sealing device associated with at least one of the handle portion and the elongate member to substantially prevent flow communication between a lumen of the elongate member and an environment external to the device, the sealing device extending proximally of a proximal-most end of the elongate member which is farthest from the end effector assembly;
   wherein the sealing device is compressed between an inner surface of the handle portion and an outer surface of the elongate member,
   wherein a portion of the sealing device comprises at least one of a silicone, a rubber, and a plastic, the portion being compressed between the inner surface of the handle portion and the outer surface of the elongate member, and
   wherein the handle portion includes a tube in flow communication with the elongate member.

19. A medical device comprising:
   a handle portion;
   an end effector assembly;
   an elongate member connecting the handle portion to the end effector assembly; and
   a sealing device associated with at least one of the handle portion and the elongate member to substantially prevent flow communication between a lumen of the elongate member and an environment external to the device;
   wherein a distal-most end of the sealing device which is closest to the end effector assembly has a radially inner surface disposed radially outward of a radially outer surface of the elongate member,
   wherein the distal-most end of the sealing device comprises at least one of a silicone, a rubber, and a plastic, wherein the handle portion includes protrusions contacting the sealing device, and wherein the end effector assembly includes biopsy forceps jaws.

20. A medical device comprising:

a handle portion;

an elongate member extending in a distal direction from the handle portion; and a sealing device associated with at least one of the handle portion and the elongate member to substantially prevent flow communication between a lumen of the elongate member and an environment external to the device;

wherein a distal-most end of the sealing device which is closest to a distal end of the elongate member has a radially inner surface disposed radially outward of a radially outer surface of the elongate member, wherein the distal-most end of the sealing device comprises at least one of a silicone, a rubber, and a plastic, wherein a proximal end of the sealing device has a first outer diameter and a distal end of the sealing device has a second outer diameter, wherein the first outer diameter is smaller than the second outer diameter, and wherein the handle portion includes a tube in flow communication with the elongate member.

21. The device of claim 20, wherein the sealing device is configured to substantially prevent fluid flow through a gap between the tube and the elongate member.

22. The device of claim 21, wherein the sealing device is disposed around the elongate member and the tube.

23. The device of claim 21, wherein the sealing device is configured to form a substantially fluid tight seal with the elongate member.

24. The device of claim 21, wherein the sealing device is configured to form a substantially fluid tight seal with the tube.

25. The device of claim 21, wherein a tip of the sealing device is configured to form a substantially fluid tight seal with the tube.

26. The device of claim 20, wherein the sealing device is disposed between an inner surface of the handle portion and an outer surface of the elongate member.

27. The device of claim 11, wherein the sealing device is compressed between an inner surface of the handle portion and an outer surface of the elongate member.

28. The device of claim 20, wherein the sealing device is configured to form a substantially fluid tight seal between the sealing device and a proximal end of the elongate member.

29. The device of claim 20, wherein the sealing device is an elastic sleeve.

30. The device of claim 20, wherein the tube is configured to be in flow communication with the environment external to the device via a proximal end of the tube.

31. The device of claim 30, wherein the sealing device is disposed on the tube.

32. The device of claim 30, wherein the sealing device is a cap at the proximal end of the tube.

33. The device of claim 11, wherein the handle portion includes protrusions contacting the sealing device.

34. The device of claim 20, wherein a portion of the sealing device which extends over the elongate member has a length, and an outer diameter of the sealing device along the length is substantially constant.

* * * * *

UNITED STATES PATENT AND TRADEMARK OFFICE
CERTIFICATE OF CORRECTION

| | |
|---|---|
| PATENT NO. | : 8,231,652 B2 |
| APPLICATION NO. | : 10/831760 |
| DATED | : July 31, 2012 |
| INVENTOR(S) | : David I. Freed et al. |

Page 1 of 1

It is certified that error appears in the above-identified patent and that said Letters Patent is hereby corrected as shown below:

Claim 7, Column 11, Line 65, "claim 3" should read as --claim 2--.

Claim 8, Column 12, Line 1, "claim 3" should read as --claim 2--.

Claim 33, Column 14, Line 25, "claim 11" should read as --claim 20--.

Signed and Sealed this
Eighteenth Day of September, 2012

David J. Kappos
*Director of the United States Patent and Trademark Office*